United States Patent [19]

Grötsch

[11] Patent Number: 5,171,856
[45] Date of Patent: Dec. 15, 1992

[54] PROCESS FOR THE PREPARATION OF 2,4,6-TRIFLUORO-1,3,5-TRIAZINE

[75] Inventor: Georg Grötsch, Bad Soden am Taunus, Fed. Rep. of Germany

[73] Assignee: Hoechst Aktiengesellschaft, Frankfurt am Main, Fed. Rep. of Germany

[21] Appl. No.: 781,240

[22] PCT Filed: Jul. 2, 1990

[86] PCT No.: PCT/EP90/01055
§ 371 Date: Feb. 24, 1992
§ 102(e) Date: Feb. 24, 1992

[87] PCT Pub. No.: WO91/00279
PCT Pub. Date: Jan. 10, 1991

[30] Foreign Application Priority Data

Jul. 4, 1989 [DE] Fed. Rep. of Germany ....... 3921918

[51] Int. Cl.$^5$ ............................................ C07D 251/28
[52] U.S. Cl. .................................................. 544/217
[58] Field of Search ........................................ 544/217

[56] References Cited

U.S. PATENT DOCUMENTS 4,329,458  5/1982  Klauke et al. .................... 544/217

FOREIGN PATENT DOCUMENTS 0035704  9/1981  European Pat. Off. .

OTHER PUBLICATIONS

C. W. Tullock et al., *J. Org. Chem.* 25, 2016–2019 (1960).

*Primary Examiner*—John M. Ford

[57] ABSTRACT

A process for the preparation of 2,4,6-trifluoro-1,3,5-triazine (cyanuric fluoride) in high purity and high yield at relatively low temperatures by reacting 2,4,6-trichloro-1,3,5-triazine (cyanuric fluoride [sic]) or mixed chlorinated/fluorinated 1,3,5-triazines with at least the equivalent amount of sodium fluoride, potassium fluoride or cesium fluoride or any desired mixture of these alkali metal fluorides in a dipolar aprotic solvent at temperatures from about 30° C. to about 110° C. and isolating the 2,4,6-trifluoro-1,3,5-triazine formed by distillation.

9 Claims, No Drawings

5,171,856

PROCESS FOR THE PREPARATION OF 2,4,6-TRIFLUORO-1,3,5-TRIAZINE

FIELD OF THE INVENTION

The invention relates to an improved process for the preparation of 2,4,6-trifluoro-1,3,5-triazine (cyanuric fluoride) in high purity and high yield by reaction of cyanuric chloride with an alkali metal fluoride in a dipolar aprotic solvent at relatively low temperatures. Cyanuric fluoride is a useful starting compound for agrochemicals, pharmaceuticals, dyes, photochemicals and optical brighteners.

PRIOR ART

It is known that cyanuric fluoride can be prepared by fluorination of cyanuric chloride with sodium fluoride in a dipolar aprotic solvent (Tullock, Coffman, J. org. Chem. 25, 2016 (1960)). In this process, cyanuric chloride is added to a suspension of sodium fluoride in sulfolane and the reaction mixture is heated from 45° C. to 248° C. The cyanuric fluoride formed is distilled off from the reaction mixture. The yield is 74% of theory. According to DE-OS 3,727,973, cyanuric fluoride is obtained by the same method. 75° C. is already mentioned here as the lowest temperature for the reaction. According to Example A and lines 11 to 15, column 2 (description), the reaction mixture must finally be heated to 220° C. in order to obtain cyanuric fluoride approximately quantitatively, i.e. in 87% yield. By-products mentioned are, inter alia, partially fluorinated substances, such as 6-chloro-2,4-difluorotriazine, which superficially indicates an incomplete reaction.

A slightly altered process is described in EP-0,035,704. Cyanuric chloride or mixed chlorinated/fluorinated 1,3,5-triazines, if desired in the form of a melt or dissolved in a dipolar aprotic solvent, are metered into a suspension of sodium fluoride in a dipolar aprotic solvent, in particular sulfolane, which is heated to 120° C. to 220° C., in particular 140° to 160° C. Cyanuric fluoride is obtained from the reaction mixture by distillation, the distillation even having to be carried out in vacuo in the presence of a component of intermediate boiling point in order to be able to remove the cyanuric fluoride formed completely.

In these known processes, the reaction mixture is kept above about 120° C. over a relatively large part of the reaction time (Tullock, Coffman) or at temperatures above 120° C., preferably at 140° C.–160° C., over the entire reaction time (EP-0,035,704). Even with the addition of phase transfer catalysts, such as, for example, 18-crown-6 (CS) 247,969, JP 61,047,465), temperatures of about 140°–400° C. are necessary in order to obtain cyanuric fluoride from cyanuric chloride using alkali metal fluorides in a dipolar aprotic solvent.

These processes thus confirm the prejudice prevailing up to now that the preparation of cyanuric fluoride (2,4,6-trifluoro-1,3,5-triazine) from cyanuric chloride and potassium fluoride requires very high reaction temperatures (HOUBEN-WEYL, volume V/3, 1962).

AIM OF THE INVENTION

An improved process for the preparation of 2,4,6-trifluoro-1,3,5-triazine (cyanuric fluoride) in high purity and high yield at relatively low temperatures.

ESSENCE OF THE INVENTION

According to the invention, it has surprisingly been found that 2,4,6-trifluoro-1,3,5-triazine (cyanuric fluoride) can advantageously be prepared in high purity and virtually quantitative yield at relatively low temperatures by reacting 2,4,6-trichloro-1,3,5-triazine (cyanuric chloride) or mixed chlorinated/fluorinated 1,3,5-triazines with at least the equivalent amount of sodium fluoride, potassium fluoride or cesium fluoride or any suitable mixture of these alkali metal fluorides in a dipolar aprotic solvent at a temperature from about 30° C. to about 110° C., preferably about 50° C. to about 105° C., in particular about 70° C. to about 100° C.

In particular, a process can be used in which cyanuric chloride and/or mixed chlorinated/fluorinated 1,3,5-triazines, the alkali metal fluoride or mixtures of the alkali metal fluorides and the dipolar aprotic solvent are mixed and allowed to heat to the desired reaction temperature (utilization of the heat of reaction liberated in the reaction) or are heated to the desired reaction temperature.

However, a process can also be used in which the cyanuric chloride is metered into the suspension of the alkali metal fluoride or the mixture of the alkali metal fluorides in a dipolar aprotic solvent as a solid, as a melt or dissolved or suspended in an inert solvent.

A further embodiment of the process according to the invention consists in metering the alkali metal fluoride or the mixture of the alkali metal chlorides into the mixture of cyanuric chloride and/or mixed chlorinated/fluorinated 1,3,5-triazines and the dipolar aprotic solvent as a solid or as a suspension in an inert solvent.

Finally, a process can also be used in which the cyanuric chloride, mixed with or dissolved in mixed chlorinated/fluorinated 1,3,5-triazines, is metered into the suspension of the alkali metal fluoride or the mixture of alkali metal fluorides in a dipolar aprotic solvent, if desired with the addition of an inert solvent.

A suitable dipolar aprotic solvent for the process according to the invention is any dipolar aprotic solvent which it is known can be employed in chlorine/fluorine exchange reactions and is inert to the halogenated triazines. Sulfolane is particularly suitable.

It is expedient to employ the alkali metal fluoride in a molar excess of about 5 to about 50%, preferably about 10 to about 20%, compared to the required equivalent amount, relative to the cyanuric chloride. Indeed, a molar excess of over 50% can be used, but there is virtually no longer any advantage associated with this and the cost-efficiency of the process suffers.

The process can be carried out both at normal pressure and at reduced pressure or elevated pressure.

Inasmuch as "inert solvents" are mentioned in the embodiments of the process mentioned above, in this case these are any suitable solvents which are inert under the reaction conditions to the starting and final compounds of the process, such as, for example, chlorobenzene, dichlorobenzene, toluene, xylene or tetrachloroethylene, or the dipolar aprotic solvent employed as the reaction medium or another dipolar aprotic solvent which is also inert under the reaction conditions to the starting and final compounds.

The particular advantage of the process according to the invention is, above all, that hitherto the reaction had to be carried out in a temperature range in which noticeable back-reaction of the cyanuric fluoride formed already takes place. Thus, in sulfolane chlorodifluorotriazine is obtained at 140° C. in 5 h in 4% yield from cyanuric fluoride in the presence of an 86% KCl/KF mixture. This is a salt mixture which is typically present after completion of the fluorination of cyanuric chloride with potassium fluoride using a 20% excess. At 190° C., a more rapid conversion of cyanuric fluoride takes place under otherwise identical conditions owing to fluorine/chlorine exchange. After about 10 h, 25% of the cyanuric fluoride is already reacted to give chlorodifluoro- and dichlorofluorotriazine (cf. Examples 1 and 2) On the other hand, this disadvantage—back-reaction of the cyanuric fluoride formed—does not occur if the reaction is carried out at temperatures up to about 110° C. (cf. Example 3). Cyanuric fluoride is thus formed rapidly and quantitatively. An equilibrium between mixed chlorinated/fluorinated triazines and cyanuric fluoride is not established.

In addition, a distinct saving of energy and thus a more economic synthesis of cyanuric fluoride is possible compared to the previous processes for the preparation of cyanuric fluoride from cyanuric chloride or mixed chlorinated/fluorinated 1,3,5-triazines with alkali metal fluorides at high temperatures.

The cyanuric fluoride is isolated in a manner customary per se by gentle distillation either in the presence of the alkali metal chloride or after separating off the salt produced, a vacuum being used if desired.

In order to obtain cyanuric fluoride of high purity, complicated separation of mixed chlorinated/fluorinated 1,3,5-triazines is not necessary since these are no longer contained in the reaction mixture after completion of the reaction.

The process according to the invention is illustrated in more detail by the examples below, without being limited thereto. (In the examples, 1,3,5-triazine is called "s-triazine".)

EXAMPLE 1 (COMPARISON EXAMPLE)

30.6 g of cyanuric fluoride are added at room temperature to a suspension of 70.3 g of KCl/KF mixture (86.5% by weight of KCl) in 138 g of dry sulfolane and the mixture is then stirred at 140° C. According to gas chromatographic analysis ("GC analysis") of the reaction mixture, 4% of the cyanuric fluoride employed has been converted into chlorodifluorotriazine after 5 hours.

EXAMPLE 2 (COMPARISON EXAMPLE)

A reaction mixture as described in Example 1 is stirred at 190° C. After 10 hours, according to GC spectrum [sic], the reaction mixture contains s-triazines in the following distribution: 75% of cyanuric fluoride, 6% of chlorodifluoro-s-triazine and 19% of dichlorofluoro-s-triazine.

EXAMPLE 3

A reaction mixture as described in Example 1 is stirred at 100° C. for 5 hours. According to GC, no fluorine/chlorine exchange can be detected in the cyanuric fluoride. The cyanuric fluoride can be quantitatively recovered.

EXAMPLE 4

46.1 g of cyanuric chloride are added at 40° C. to a suspension of 52.3 g of potassium fluoride in 175 g of dry sulfolane and the mixture is heated to 80° C. in the course of 20 minutes. After stirring for 80 minutes at this temperature, the yield according to GC is 99.2% of theory.

EXAMPLE 5

67.5 g of cyanuric chloride are mixed at 30° C. with a suspension of 104.6 g of potassium fluoride in 300 g of sulfolane in a heat-insulated reaction vessel. The reaction mixture heats uniformly to 97° C. within 10 minutes. GC checking shows that cyanuric chloride has already reacted quantitatively to give cyanuric fluoride.

EXAMPLE 6

To a suspension of 384 g of potassium fluoride in 700 g of sulfolane at 100° C., a solution of 369 g of cyanuric chloride in 500 g of sulfolane, also at 100° C., is added dropwise in the course of 2 hours. GC checking of the reaction mixture shows that cyanuric chloride has reacted quantitatively to give cyanuric fluoride. Cyanuric fluoride is then distilled off at a pressure of 500 to 100 mbar. The yield is 257 g (95% of theory); purity: 99.4 area % (GC).

EXAMPLES 7 TO 10

The procedure is analogous to Example 6. Amounts employed and yields are summarized in the following table.

| Example | NaF [g] | KF [g] | CsF [g] | Cyanuric chloride [g] | Sulfolane [g] | Cyanuric fluoride [g] |
|---|---|---|---|---|---|---|
| 7 | 302 | — | — | 369 | 1000 | 251 |
| 8 | 134 | 13 | — | 184 | 550 | 122 |
| 9 | — | 191 | 19 | 184 | 700 | 126 |
| 10 | 139 | — | 14 | 184 | 550 | 125 |

EXAMPLE 11

30 g of a mixture of cyanuric chloride (8.6% by weight), dichlorofluoro-s-triazine (9.5% by weight), chlorodi-fluoro-s-triazine (16.4% by weight) and cyanuric fluoride (65.5% by weight) are added to 20 g of KF in sulfolane and the mixture is stirred at 60° to 70° C. After 40 minutes, according to GC all chlorine-containing triazines have been converted into cyanuric fluoride.

EXAMPLE 12

A mixture of 184 g of cyanuric chloride, 209 g of potassium fluoride and 900 g of sulfolane are heated to 100° C. for 4 hours in a 2 l autoclave. An overpressure of about 0.8 bar is established. According to GC, quantitative conversion of the cyanuric chloride to cyanuric fluoride took place.

EXAMPLE 13

209 g of potassium fluoride are metered into 184 g of cyanuric chloride in 800 g of sulfolane at 100° C. in the course of 1 hour and the mixture is then stirred at this temperature for a further hour. According to GC, the conversion of the cyanuric chloride to cyanuric fluoride is quantitative.

EXAMPLE 14

184 g of cyanuric chloride are reacted with 192 g of potassium fluoride analogously to Example 6. After filtering off with suction the KCl/KF mixture obtained after completion of the reaction and washing it with 600 g of chlorobenzene, cyanuric fluoride is distilled off from the mother liquor. The yield is 129 g (96% of theory).

Purity: 99.9 area % (GC).

The boiling point of the cyanuric fluoride obtained and isolated according to Examples 6 to 10 and 14 is 72.5 to 3.0° C.

EXAMPLE 15 (COMPARISON EXAMPLE)

A solution of 111 g of cyanuric chloride in 60 g of sulfolane at 140° C. is metered in the course of 15 minutes into a suspension of 90.8 g of NaF in 104 g of sulfolane at 160° C. and the mixture is subsequently stirred at 190° C. for 1 hour, altogether about ¾ of the total fluoride distilling over. The residual product is separated off at 500 mbar to 50 mbar. The yield is 74.2 g (92% of theory). According to GC, the product has the following composition: cyanuric fluoride 97.7%, chlorodifluorotriazine 1.5%, dichlorofluorotriazine 0.5% and unknown compounds 0.3%.

I claim:

1. A process for the preparation of 2,4,6-trifluoro-1,3,5-triazine (cyanuric fluoride) in high yield and high purity at relatively low temperatures, which comprises reacting 2,4,6-trichloro-1,3,5-triazine (cyanuric chloride) or mixed chlorinated/fluorinated 1,3,5-triazines with at least the equivalent amount of sodium fluoride, potassium fluoride or cesium fluoride or any desired mixture of these alkali metal fluorides in a dipolar aprotic solvent at temperatures from about 30° C. to about 110° C. and isolating the 2,4,6-trifluoro-1,3,5-triazine formed by distillation.

2. The process as claimed in claim 1, wherein the reaction is carried out at temperatures from about 50° C. to about 105° C.

3. The process as claimed in claim 1, wherein the reaction is carried out at temperatures of about 70° C. to about 100° C.

4. The process as carried out in claim 1, wherein cyanuric chloride and/or mixed chlorinated/fluorinated 1,3,5-triazines, the alkali metal fluoride or mixtures of the alkali metal fluorides and the dipolar aprotic solvent are mixed and allowed to heat to the desired reaction temperature or are heated to the desired reaction temperature.

5. The process as claimed in claim 1, wherein the cyanuric chloride is metered into the suspension of the alkali metal fluoride or the mixture of the alkali metal fluorides in a dipolar aprotic solvent as a solid, as a melt or dissolved or suspended in an inert solvent.

6. The process as claimed in claim 1, wherein the alkali metal fluoride or the mixture of the alkali metal fluorides is metered into the mixture of cyanuric chloride and/or mixed chlorinated/fluorinated 1,3,5-triazines and the dipolar aprotic solvent as a solid or as a suspension in an inert solvent.

7. The process as claimed in claim 1, wherein mixed chlorinated/fluorinated 1,3,5-triazines or the cyanuric chloride, mixed with or dissolved in mixed chlorinated/fluorinated 1,3,5-triazines, is/are metered into the suspension of the alkali metal fluoride or the mixture of the alkali metal fluorides in a dipolar aprotic solvent, if desired with the addition of an inert solvent.

8. The process as claimed in claim 1, wherein the alkali metal chlorides produced are separated off before the isolation of the 2,4,6-trifluoro-1,3,5-triazine.

9. The process as claimed in claim 1, which process is carried out at normal pressure, reduced pressure or elevated pressure.

* * * * *